United States Patent [19]

Sisto et al.

[11] Patent Number: 4,728,725

[45] Date of Patent: Mar. 1, 1988

[54] RETRO-INVERTED PEPTIDES ANALOGUES OF BRADYKININ POTENTIATOR BPP$_{5a}$

[75] Inventors: Alessandro Sisto, Rome; Antonio S. Verdini, Monterotondo; Antonino Virdia, Rome, all of Italy

[73] Assignees: Enichem, S.p.A.; Eniricerche, S.p.A., both of Milan, Italy

[21] Appl. No.: 811,487

[22] Filed: Dec. 20, 1985

[30] Foreign Application Priority Data

Dec. 21, 1984 [IT] Italy ............................. 24200 A/84

[51] Int. Cl.$^4$ .......................... C07K 7/18; C07K 7/02
[52] U.S. Cl. .................................. 530/314; 530/323; 530/330; 530/332
[58] Field of Search ................ 530/314, 323, 330, 332

[56] References Cited

U.S. PATENT DOCUMENTS 4,522,752   6/1985   Sisto et al. ............................ 530/314

OTHER PUBLICATIONS

Chem. Abstr. vol. 66, (1966) 26298r.

Primary Examiner—Delbert R. Phillips
Attorney, Agent, or Firm—Hedman, Gibson, Costigan & Hoare

[57] ABSTRACT

Retro-inverted peptides, analogues of Bradykinin Potentiator Pentapeptide (BPP$_{5a}$), definable by the general formula (I)

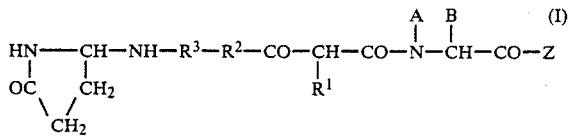

useful as antihypertensives and diagnostics.

3 Claims, No Drawings

RETRO-INVERTED PEPTIDES ANALOGUES OF BRADYKININ POTENTIATOR BPP$_{5a}$

The present invention relates to novel retro-inverted peptides, analogues of Bradykinin Potentiator Pentapeptide (BPP$_{5a}$), pharmacologically active, and long-lasting in vivo, of general formula (I)

$$\text{HN}\underset{\underset{\underset{CH_2}{\diagdown\diagup}}{OC\quad CH_2}}{\text{—CH—NH—R}^3\text{—R}^2\text{—CO—}\overset{A}{\overset{|}{CH}}\text{—CO—}\overset{}{\text{N}}\text{—}\overset{B}{\overset{|}{CH}}\text{—CO—Z}} \quad (I)$$
$$\qquad\qquad\qquad\qquad\qquad\qquad\qquad R^1$$

useful as antihypertensives and diagnostics.

The renin-angiotensin-aldosterone system has been recently, recognized as one of the factors of primary importance in determining hypertension arising.

The action of enzyme renin on a pseudoglobulin of blood plasma produces a peptide, angiotensin I, which is converted into the octapeptide angiotensin II by the angiotensin conversion enzyme (ACE).

Angiotensin II exerts a powerful vasoconstrictor action, which produces a blood pressure increase;

Angiotensin Conversion Enzyme is also responsible the inactivation of bradykinin, a nonapeptide with powerful hypotensive action.

The result of this twofold action is an increase in arterial pressure.

Compounds inhibiting angiotensin conversion enzyme can be useful as antihypertensive agents in the management of renal hypertension, of malignant hypertension, and of essential hypertension.

Said inhibitors can also be used as diagnostics for the determination of the involvement degree of renin-angiotensin system in the arising and maintainment of hypertensive states.

Peptides potentiating the activity of bradykinin, and inhibiting angiotensin conversion enzyme have been isolated from the poison of snake Bothrops jararaca.

Among these, particularly interesting has resulted pentapeptide Glp-Lys-Trp-Ala-Pro (BPP$_{5a}$).

Said peptide is a powerful inhibitor of angiotensin conversion enzyme in vitro, causes a regression of renovascular hypertension, experimentally caused in rats, potentiates in vivo the activity of bradykinin directly injected into coronary arteries, and, when directly injected into brain, inhibits the hypertensive action of angiotensin I.

BPP$_{5a}$ behaves as "mixed inhibitor", both competitive and not competitive, in agreement with the hypothesis that it can recognize two receptor sites of conversion enzyme: in the one, it bonds itself to the C-ending tripeptide, and in the other to the N-ending dipeptide.

Structure-function studies with a set of BPP$_{5a}$ analogues have evidenced that:

(a) only C-ending tripeptide bonds itself to the same active site on the enzyme, onto which whole decapeptide angiotensine I bonds itself;
(b) the enzymatic activity is expressed only when C-ending carboxy is free;
(c) the enzyme does not hydrolyse peptides containing a dicarboxy aminoacid residue in position 5, or an iminoacid, such as e.g., proline, in position 4;
(d) substrates containing a tryptophan or a phenylalanine, in position 3, bond themselves with a greater affinity for the enzyme than substrates having different residues in the same position;
(e) the introduction of aminoacids with D-configuration, in position 3, causes the loss of inhibiting activity.

As the biological activity in vivo is one of the requisites essential for the use of peptidic inhibitors as drugs, the extreme lability of BPP$_{5a}$ and analogues thereof to angiotensin conversion enzyme and to peptidases, jeopardizes the use thereof in pharmacology and in clinics.

In fact, 15 minutes of preincubation with the enzyme are sufficient to have a complete loss of BPP$_{5a}$ inhibiting activity [Ondetti, M. A. et al., Annual Reports in Medicinal Chemistry, Chap. 9,82 (1978); Ondetti, M. A. et al., Drug action and Design: Mechanism Based Enzyme Inhibitors, Ed. Kalman, by Elsevier North Holland Inc., p. 271 (1979); Cushman, D. W. et al., Progress in Medicinal Chemistry, 17, Chap. 2, 42 (1980)].

It has been found now that it is possible to overcome the disadvantages of the known technique by means of the use of peptides showing a stability in vivo to the hydrolytic action of peptidase enzymes.

The purpose of the present invention are hence retroinverted peptides analogues of Bradykinin Potentiating Pentapeptide (BPP$_{5a}$), useful as antihypertensives and diagnostics. In particular, retro-inverted peptides according to the present invention are definable by the general formula $$\text{HN}\underset{\underset{\underset{CH_2}{\diagdown\diagup}}{OC\quad CH_2}}{\text{—CH—NH—R}^3\text{—R}^2\text{—CO—}\overset{A}{\overset{|}{CH}}\text{—CO—}\overset{}{\text{N}}\text{—}\overset{B}{\overset{|}{CH}}\text{—CO—Z}} \quad (I)$$
$$\qquad\qquad\qquad\qquad\qquad\qquad\qquad R^1$$

wherein
R$^3$ and R$^2$ represent an aminoacid residue with D-configuration;
R$^1$ represents the side chain of one of aminoacid residues present in the chains of natural peptides or synthetic analogues of the same;
A represents a hydrogen atom, an alkyl group with a number of carbon atoms from one to seven, an aryl group, an arylalkylene or hydroxyalkylene group with a number of carbon atoms of from one to seven;
B represents a hydrogen atom, an alkyl group with a number of carbon atoms of from one to seven, an aryl, arylalkylene, hydroxyalkylene, guanidylalkylene, aminoalkylene, alkyloxyalkylene, acylaminoalkylene, imidazolylalkylene, indolylalkylene, mercaptoalkylene alkylmercaptoalkylene, carbamoylalkylene, carboxyalkylene, alkylcarbamoylalkylene or alkyloxycarbonylalkylene group.

A and B, taken together, can be a —(CH$_2$)$_m$— residue closed to form a ring on carbon and nitrogen atoms onto which they are bonded, with an atom of —(CH$_2$)$_m$— bridge being directly linked to an o-benzyl, or -S-phenyl group; m can be equal to 3 or 4; Z represents a hydroxy, alkylhydroxy or amino group.

According to the present invention, the compounds of formula (I) have their peptidic bonds, between the residues of aminoacids 1 and 2, 2 and 3, 3 and 4, suitably inverted:

The retro-inversion of said bonds allows the tridimensional orientation of the side chains of peptide to be maintained, allowing a correct bond to the conversion enzyme's active site, and potentiates the biological activity of the analogue, by improving its in-vivo stability.

The inversion of three peptidic bonds in the sequence involves the modification of the two aminoacid residues in positions 1 and 4, and the contemporaneous inversion of chirality of residues 2 and 3.

In particular, the residue of pyroglutamic acid is transformed into a geminal diamino residue of structure:

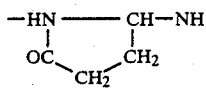

and the residue in position 4 is transformed into a residue of malonyl or 2-substituted malonyl residue of general formula —OC—CHR$^1$—CO—, wherein R$^1$ has the above reported meaning.

Whilst the incorporation of malonyl or 2-substituted malonyl residues into the peptide backbone does not show any difficulties, that of gem-diamino residues requires particular and delicate handlings.

According to the present invention, the introduction of gem-diamino residue in the peptide backbone is carried out by using reactant I,I-bis-(trifluoroacetoxy)-iodobenzene, according to the method as disclosed in the Italian Pat. Application No. 25 755A/81filed on Dec. 22, 1981.

Such an operating way allows retro-inverted analogues of peptides with high biological activity to be very easily synthetized, both in homogeneous phase, and on insoluble polyamidic matrices.

According to the present invention, retro-inverted peptides of formula (I) are synthetized by means of a process comprising:

(a) condensing, in liquid phase, in inert organic solvent, in the presence of dicyclohexylcarbodiimide (DCC) and hydroxybenzotriazole (HOBt), a compound of formula

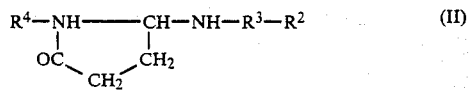

wherein R$^4$ represents a hydrogen atom, an alkoxycarbonyl or arylalkyloxycarbonyl residue, R$^3$ and R$^2$ represent an aminoacid residue with D-configuration, wherein the reactive residue in side chain is suitably protected with a protecting group selected according to the known art, with a compound of formula (III)

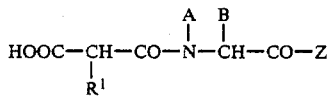

wherein R$^1$, A, B and Z have the above reported meaning, (b) removing the protecting groups from the so-obtained compound (I), (c) separating and purifying the so obtained compound (I).

According to the present invention, in stage (a) the condensation reaction is carried out by suspending in an inert organic solvent the compounds of formula (I) and (II), in the presence of condensation agents, such as DCC and HOBt.

The temperatures at which stage (a) is carried out are comprised within the range of from −30° C. to 10° C., and the corresponding reaction times range from 2 to 4 hours.

The reaction is generally carried out at a temperature of 0° C., for a 2.5 hours time period.

At the end of said reaction, the removal is carried out, in stage (b), of the protective groups of reactive functional groups in side chain of peptide of formula (I).

Step (b) is typically carried out by hydrolysis of compound (I) with a 0.5N sodium hydroxide solution in a mixture of water/dioxane (1:1, v/v) (pH=12.5), at room temperature, over about 16 hours.

The separation and purification of reaction product (I) is carried out by means of processes known in peptide isolating art, such as, e.g.: extraction, counter-current distribution, precipitation, crystallization and chromatography.

The identity of the products is demonstrated by nuclear magnetic resonance spectroscopy analysis.

The purity of the products is verified by means of high pressure reverse phase chromatographic (RP-HPLC) analysis, using the following eluent systems: H$_2$O/MeCN, TFA at 0.1% in aqueous solution/MeCN; and thin-layer chromatographic analysis in silica gel, using the following eluent systems: n-butanol:acetic acid:water (4:1:1); chloroform:methanol:acetic acid (85:10:5); n-butanol:isopropanol:NH$_4$OH in water:ethyl acetate (1:1:5:1), organic phase.

The synthesis of the fragments of general formula (II) and (III) is carried out by using the peptide synthesis methods as described by Bodanszki, M. and Ondetti, M. A. [Peptide Synthesis, Interscience, New York, 1976; and The Peptides, Vol. 1, Gross, E. and Meinhofer, L. Publishers, Academic Press, New York (1979)].

The inhibition of angiotensin conversion enzyme by the compounds corresponding to general formula (I) is measured, in vitro, with the enzyme isolated from rabbit lungs according to the method by Cushman and Cheung [Biochem.-Pharmacol., 20, 1637, (1971)].

In Table 1 the values of I$_{50}$ (μM) obtained by using the retroinverted analogues and natural not-modified peptide, which is used as the comparison term, are reported.

TABLE 1

| Peptide | I$_{50}$ (μM) |
|---|---|
| (A) Glp—Lys—Phe—Ala—Pro | 0.13 (tech. papers = 0.07) |
| (B) gGlp—Dlys—DPhe—(S)m Ala—Pro—(4-allo—SPh)—OH | 750 × 10$^{-2}$ |
| (C) gGlp—DLys—DPhe—(R)m Ala—Pro—(4-allo—SPh)—OH | 1200 × 10$^{-3}$ |

The stability of peptides of formula (B) and (C) has been verified by determining the resistance of said peptides to the angiotensin conversion enzyme and to peptidases.

The results show that said peptides and in particular analogue B are resistant towards the enzymatic degradation after 3 hours of incubation.

The following experimental Examples are illustrative and not limitative for the invention.

EXAMPLE 1

Synthesis of gem-Pyroglutamyl-D-lysyl-D-phenylalanyl-(R,S)2-methylmalonyl-proline (4-allothiophenyl), Glp-D-Lys-D-Phe-(R,S)mAla-Pro(4-allo-S-Ph)

Synthesis of N,N'-Bis(benzyloxycarbonyl)-(L-5-aminopyrrolydin-2-one: z-gGlp-H-Z Into a glass flask, with capacity of 50 ml, provided with stirrer, 10 ml of anhydrous toluene and 2 g (7.59 mmol) of benzyloxycarbonyl-L-pyroglutamic acid are charged.

The suspension is kept stirred up to complete dissolving of the product. To this solution are then added, under stirring, and under a nitrogen atmosphere, 1.64 ml (7.59 mmol) of diphenylphosphonylazide.

The mixture is heated up to a temperature of 80° C. and then 1.05 ml (7.59 mmol) of triethylamine dissolved in 5 ml of anhydrous toluene are added dropwise and over a 2 hours time period thereto.

At the end to the reaction mixture 0.86 ml (8.35 mmol) of benzyl alcohol are added dropwise and over a time period of about 2 hours.

The so-obtained mixture is kept under stirring until room temperature (20° C.–25° C.) is reached.

The precipitate formed is filtered off from the reaction mixture, is washed with 20 ml of cold toluene, and dried in vacuo.

A recrystallization of the raw product so obtained, from ethyl acetate (EtOAc), allows a crystalline product to be obtained with a 90% yield.

The product shows: mp 150° C.–151° C. $[\alpha]_{25}^{589} = -36.7°$ Cl, N,N-dimethylformamide (DMF).

The purity of the product is confirmed by chromatographic analysis (t.l.c. and h.p.l.c.) and $^1$H-nmr.

Synthesis of "L"-5-aminopyrrolidin-2-one formate:aGlp-H.HCOOH

To a solution of 1 g (2.71 mmol) of Z-gGlp-H-Z in 5 ml of DMF, 0.34 g (10.84 mmol) of ammonium formate dissolved in 10 ml of methanol (MeOH) and 50 mg of palladium sponge are added.

The solution is kept at 25° C. over 10 minutes. At the end of such time period, the solvent is evaporated off from the reaction mixture, and the residue is freeze-dried twice from H$_2$O-dioxane.

0.36 g (95%) of desired product are obtained. The melting point is 106°–107° C.
$[\alpha]_{25}^{589} = +6.0°$ (Cl, DMF).

Synthesis of N$^\alpha$-tert.butyloxycarbonyl-D-lysyl-(N$^\epsilon$-trifluoroacetyl)-gem-pyroglutamic acid:Boc-D-Lys-(N$^\epsilon$-TFA)-gGlp 3.42 g (10 mmol) of Boc-D-Lys (N$^\epsilon$TFA) are dissolved in 15 ml of CH$_2$Cl$_2$. To said solution, cooled at 0° C. and kept under stirring, 1.48 g (11 mmol) of N-hydroxibenzotriazole (HOBt) dissolved in 5 ml of DMF and 2.06 g (10 mmol) of N,N'-dicyclohexylcarbodiimide (DCC) dissolved in 5 ml of CH$_2$Cl$_2$ are added.

After 30 minutes, the ice bath is removed, and reaction mixture is kept under stirring over further 30 minutes. At the end of said time period, to the solution 2.04 g (10 mmol) of gGLp-TFA and 1.06 g (10 mmol) of N-methylmorpholine (NMMU) are added.

The mixture is reacted at a temperature of 25° C. over 1 hour.

At the end, dicyclohexylurea (DCU) is filtered off and washed with 10 ml of CH$_2$Cl$_2$ and the filtrate is evaporated to dryness.

The resulting oil is dissolved with 50 ml of EtoAc and extracted with 50 ml of sodium bicarbonate at 5% and with a sodium chloride saturated solution.

The so-obtained organic solution is dried over magnesium sulphate, after having evaporated off the solvent.

The so-obtained solid residue (yield 70%) is triturated with ethyl ether, is filtered and dried.

The product shows a melting point of 145°–146° C. $[\alpha]_{25}^{589} = +38.0°$ (C=1 in MeOH).

The chromatographic analysis (t.l.c. and h.p.l.c) does not show traces of impurities.

Elemental analysis for C$_5$H$_{10}$O$_3$N$_2$:
Theoretical: C, 41.09%; H, 6.89%; N, 19.17%.
Found: C, 40.95%; H, 6.96%; N, 19.48%.

IR,H.n.m.r. and mass spectra are in accordance with the structure of the compound.

Synthesis of N$^\alpha$-benzyloxycarbonyl-D-phenylalanyl-D-lysyl (N$^\epsilon$-trifluoroacetyl) gem-pyroglutamic acid: gGLp-D-Lys-(TFA)-D-Phe-Z 0.365 g (1.22 mmol) of Z-D-Phe-OH are dissolved in 20 ml of CH$_2$Cl$_2$.

To said solution, cooled at 0° C. and under strong stirring, are then added 0.175 g (1.22 mmol) of HOBt in 5 ml of DMF and 0.275 g (1.33 mmol) of DCC in 5 ml of CH$_2$Cl$_2$.

After 30 minutes, the ice bath is removed, and the reaction mixture is kept under stirring, for further 30 minutes.

At the end of said time period, to the solution 0.400 g (1.22 mmol) of gGlp-D-Lys(THF)-H.HCl in 5 ml of DMF and 134 μl (1.22 mmol) of NMM) are added. After 1 hour, the reaction mixture is filtered, washing DCU with CH$_2$C$_{12}$, and evaporated to dryness.

The resulting oil is dissolved with ethyl acetate and kept under stirring over 10 minutes.

The insoluble residue is recovered by filtration off from the reaction mixture, is washed with NaCl-saturated water, water and ethyl ether.

After drying in vacuo, the product is washed with a solution of sodium bicarbonate at 5%, water, and finally dried in vacuo.

0.200 g of product (30%) are obtained, with a melting point of 215°–220° C. (decomposition).
$[\alpha]_{20}^{589} = +29.2°$ (C=1, in MeOH).

IR and $^1$H-nmr spectra are in accordance with compound's structure.

Synthesis of D-phenylalanyl-D-lysyl (N$^\epsilon$-trifluoro-acetyl)-gem pyroglutamic acid:gGlp-D-Lys(TFA)-D-Phe-H.COOH.

To a solution of 0.200 g (0.33 mmol) of gGlp-D-Lys(TFA)-D-Phe-Z in 5 ml of DMF 0.83 g (1.32 mmol) of HCOONH$_4$ dissolved in 0.5 ml of methanol/water (10/1 v/v) and 0.250 g of catalyst palladium on charcoal are added.

The reaction is carried out at a temperature of 25° C. over 15 minutes.

The catalyst is then filtered off from reaction mixture, and the solution is evaporated to dryness.

The residue is dissolved with 0.5 ml of dioxane-H$_2$O (50/50 v/v) and is then freeze-dried.

0.140 g of pure product are obtained, with yield 85%.

Synthesis of methyl ether of gem-pyroglutamyl-D-lysyl-(Nε-trifluoroacetyl)-D-phenylalanyl-(R,S)2-methylmalonyl-proline (4-allo-thiophenyl): gGlpD-Lys (TFA)-D-Phe-(Rhe-(R,S)$_m$-Ala-Pro-(4-allo-S-Ph) OMe 0.137 g (0.40 mmol) of (R,S)$_m$ Ala-Pro-(4-allo-S-Ph)-OMe are dissolved in 20 ml of DMF.

To said solution, cooled at about 0° C., 0.140 g (0.27 mmol) of gGlp-D-Lys(TFA)-D-Phe-H.HCOO, 32.7 μl (0.3 mmol) of NMM, 0.058 g (0.4 mmol) of HOBt and 0.083 g (0.4 mmol) of DCC dissolved in 10 ml of CH$_2$Cl$_2$ are added.

After one hour, the ice bath is removed, and the mixture is kept under vigorous stirring over 2.5 hours.

At the end of the reaction DCU is filtered off, and is washed with DMF. The solutions combined are evaporated to dryness under reduced pressure.

The residue is then resuspended in 15 ml of NaHCO$_3$, pH 8.0, and the mixture is kept under stirring over about 20 minutes.

The mixture is dissolved with 50 ml of ethyl acetate and the organic layer which separates off is washed with 10 ml of H$_2$O, 10 ml of bicarbonate at 5%, and 10 ml of water.

The organic solution is finally dried over MgSO$_4$, ethyl acetate is evaporated to dryness and finally the so-obtained residue is triturated with ethyl ether, filtered and dried.

0.150 g of white powdered product with melting point 120°-122° C. are recovered (yield 57%). $[\alpha]_{25}^{589} = +24.8°$ (C=0.5, MeOH).

The chromatographic analysis does not show traces of impurities, and $^1$H-nmr spectrum confirms the structure of the molecule.

Synthesis of gem-Pyroglutamyl-D-lysyl-D-phenyl-Alanyl-(R,S)Z-methylmalonyl-proline (4-allo-thiophenyl): gGlp-D-Lys-D-Phe-(R,S) m Ala-Pro-(4-allo-s-ph)-OH 0.0075 g (0.08 mmol) of gGlp-D-Lys (TFA)-D-Phe-(R,S)- -m Ala-Pro-(4-allo-S-Ph)-OMe are dissolved in 15 ml of a H$_2$O-dioxane mixture (50/50, v/v), and hydrolized with 1 ml of a 0.5N NaOH solution in water/dioxane (50/50, v/v) at pH 12.5 over about one night. At the end of the reaction, the mixture is neutralized with 0.5N HCl.

The solvent is separated from the reaction mixture by evaporation, and the residual liquid is freeze-dried after dilution with water.

The desired product is isolated by means of preparative high pressure liquid chromatography, with stationary phase constituted by Lichropep R-18, 25–40μ (Merck), using TFA 0.1%—MeCn 38.8% and water as the eluent.

Three fractions of total weight 0.05 g (yield 85%) are obtained, after evaporation of the organic solvents, and freeze-drying.

The first fraction (0.021 g) corresponds to diastereoisomer gGlp-D-Lys-D-Phe-(S)-m Ala-Pro (4-allo-S-Phe)-OH, the third fraction (0.011 g) corresponds to diastereoisomer containing the residue (R) mAla-OH and the second fraction (in order of elution from the column) of 0.018 g, corresponds to a mixture of the two peptidic diastereoisomers in relative proportions not determined.

The product isolated in the first fraction has specific rotation $[\alpha]_{25}^{589} = +32.3°$ (C=0.6, H$_2$O) The product isolated in the second fraction has specific rotation $[\alpha]_{25}^{589} = +19.2°$ (C=0.5, H$_2$O)

$^1$H-nmr spectra of each one of the two fractions confirm the structure of the molecules.

We claim:

1. Retro-inverted peptides which are analogues of Bradykinin Potentiating Pentapeptide having the general formula:

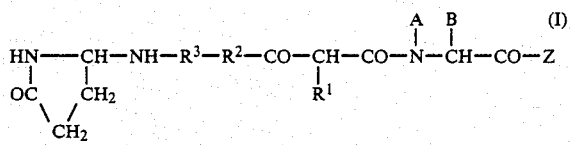

effective as antihypertensives and, resistant to angiotensin conversion enzyme, wherein:

R$^3$ is D-Lysine, R$^2$ is D-Phenylanine and

R$^1$ represents the side chain of aminoacid residues present in the chains of natural peptides;

A and B, taken together, are a —(CH$_2$)$_m$—residue closed to form a ring on the nitrogen and caron atoms to which they are bonded, with one carbon atom of the —(CH$_{2pl}$ )$_m$—bridge being directly bonded to an o-benzyl or to an -S-phenyl group;

m is equal to 3 or 4; and z represents a hydroxy, alkylhydroxy or amino group.

2. Peptide having the following formula

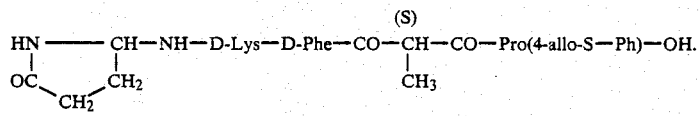

3. Peptide having the following formula

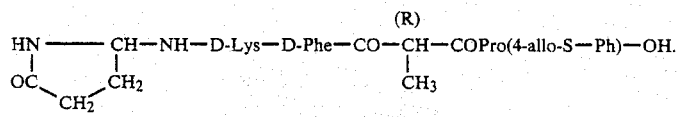

* * * * *